(12) United States Patent
Xue et al.

(10) Patent No.: US 11,118,198 B2
(45) Date of Patent: Sep. 14, 2021

(54) METHOD AND DEVICE FOR FERMENTATION INTEGRATED WITH SEPARATION AND PURIFICATION OF ALCOHOLS

(71) Applicant: Dalian University of Technology, Liaoning (CN)

(72) Inventors: Chuang Xue, Dalian (CN); Chao Zhu, Dalian (CN); Lijie Chen, Dalian (CN)

(73) Assignee: Dalian University of Technology, Liaoning (CN)

( * ) Notice: Subject to any disclaimer, the term of this patent is extended or adjusted under 35 U.S.C. 154(b) by 385 days.

(21) Appl. No.: 15/737,796

(22) PCT Filed: Jun. 15, 2016

(86) PCT No.: PCT/CN2016/085818
§ 371 (c)(1),
(2) Date: Dec. 19, 2017

(87) PCT Pub. No.: WO2017/214873
PCT Pub. Date: Dec. 21, 2017

(65) Prior Publication Data
US 2019/0093134 A1 Mar. 28, 2019

(51) Int. Cl.
| | |
|---|---|
| *C12P 7/16* | (2006.01) |
| *C12P 7/28* | (2006.01) |
| *B01D 71/02* | (2006.01) |
| *B01D 3/00* | (2006.01) |
| *B01D 3/14* | (2006.01) |
| *C12P 7/06* | (2006.01) |
| *C07C 45/78* | (2006.01) |
| *C07C 45/81* | (2006.01) |
| *B01D 5/00* | (2006.01) |
| *B01D 61/36* | (2006.01) |
| *B01D 71/70* | (2006.01) |
| *C07C 29/76* | (2006.01) |

(52) U.S. Cl.
CPC ............... *C12P 7/16* (2013.01); *B01D 3/002* (2013.01); *B01D 3/145* (2013.01); *B01D 5/0045* (2013.01); *B01D 61/362* (2013.01); *B01D 71/028* (2013.01); *B01D 71/70* (2013.01); *C07C 29/76* (2013.01); *C07C 45/786* (2013.01); *C07C 45/81* (2013.01); *C12P 7/065* (2013.01); *C12P 7/28* (2013.01); *B01D 2257/70* (2013.01); *B01D 2311/2688* (2013.01)

(58) Field of Classification Search
CPC .... C12P 7/16; C12P 7/065; C12P 7/28; B01D 3/002; B01D 3/145; B01D 5/0045; B01D 61/362; B01D 71/028; B01D 71/70; B01D 2257/70; B01D 2311/2688; C07C 29/76; C07C 45/786; C07C 45/81
USPC .......................................................... 435/41
See application file for complete search history.

(56) References Cited

FOREIGN PATENT DOCUMENTS

CN 10211854 * 2/2013

OTHER PUBLICATIONS

Chuang et al., A Novel In Situ Gas Stripping-Pervaporation Process Integrated With Acetone-Butanol-Ethanol Fermentation for Hyper n-Butanol Production, Biotechnology and Bioengineering, vol. 113, No. 1, Jan. 31, 2016, pp. 120-129.*
Di Cai et al., Gas stripping-pervaporation hybrid process from energy-saving product recovery from acetone-butanol-ethanol (ABE) fermentation broth, Chemical Engineering Journal, vol. 287, (Mar. 1, 2016), pp. 1-10.*
Yakovlev et al., Separation of diluted butanol-water solutions via vapor phase by organophilic membranes based on high permeable polyacetylenes, Journal of Membrane Science vol. 434, (2013), pp. 99-105.*

* cited by examiner

*Primary Examiner* — Jennifer M. H. Tichy
(74) *Attorney, Agent, or Firm* — Westerman, Hattori, Daniels & Adrian, LLP

(57) ABSTRACT

The disclosure relates to a method for fermentation integrated with separation and purification of acetone, butanol, and ethanol (ABE) or butanol alone, comprising the following steps: 1) obtaining ABE by fermentation using an acetone-butanol-producing bacterium or obtaining butanol using a butanol-producing bacterium; 2) using a "vapor-stripping-vapor-permeation" method (briefly VSVP) for online separation and purification of ABE or purifying butanol from the fermentation broth; wherein the VSVP method comprises the following steps: introducing a gas bubble into the fermentation broth comprising active cells for fermentation to vaporize ABE or Butanol; subjecting the gas along with the vaporized ABE or Butanol to a membrane separation unit to pass through the membrane; recovering ABE or Butanol, or subjecting ABE or Butanol to a next separation device. By using the disclosed method, production, separation, and purification efficiency of ABE or butanol are improved with saved energy consumption and without increasing equipment investment.

14 Claims, 1 Drawing Sheet

METHOD AND DEVICE FOR FERMENTATION INTEGRATED WITH SEPARATION AND PURIFICATION OF ALCOHOLS

TECHNICAL FIELD

The present disclosure relates to a method for integrating fermentation process with butanol, acetone and ethanol (or only butanol) recovery. It belongs to the biotechnology area.

BACKGROUND

Butanol and acetone are considered as potential liquid fuels and important chemicals in medical and food industry, which could be produced by microbial fermentation (Dune, P. Biobutanol: an attractive biofuel. Biotechnol. J. 2:1525-1534, 2007). The final butanol concentration in fermentation broth using *Clostridium acetobutylicum* or *Clostridium beijerinckii* is difficult to exceed 2.0% (w/v). Furthermore, the boiling point of butanol is 117.7° C., which is higher than that of water (100° C.). Therefore, the conventional recification and distillation methods for butanol recovery are energy intensive, and are not economic for industrial scale up (Matsumura, M., Kataoka, H., Sueki, M., Araki, K. Energy saving effect of pervaporation using oleyl alcohol liquid membrane in butanol purification. Bioprocess Eng. 3: 93-100, 1988).

Alternative separation techniques such as liquid-liquid extraction, gas stripping, adsorption and pervaporation could be integrated with butanol fermentation process, with improved butanol production and reduced inhibitory effects to cells by removing butanol from the fermentation broth (Xue C, Zhao J B, Chen U, Bai F W, Yang S T, Sun J X. Integrated butanol recovery for an advanced biofuel: current state and prospects. Appl Microbiol Biotechnol, 2014, 98:3463-3474; Qureshi, N., Meagher, M. M., Huang, J. C., Hutkins, R. W. Acetone butanol ethanol (ABE) recovery by pervaporation using silicalite-silicone composite membrane from fed-batch reactor of *Clostridium acetobutylicum*. J. Membr. Sci. 187: 93-102, 2001). However, the main problems of these above-mentioned techniques are low butanol recovery concentration and low efficiency, and further processes are needed to optimize the techniques and to concentrate the product by dehydration.

DETAILED DESCRIPTION

To solve the problems above, the present disclosure uses a vapor-stripping-vapor-permeation process integrated with fermentation of ABE (acetone-butanol-ethanol) or butanol to produce ABE or Butanol, with online ABE or Butanol recovery during the fermentation process.

The present disclosure involves the following aspects.

1. A method for fermentation integrated with separation and purification of acetone, butanol, and ethanol (ABE) or butanol alone, comprising the following steps:

1) obtaining ABE or Butanol by fermentation using an acetone-butanol-producing bacterium or a butanol-producing bacterium;

2) using a "vapor-stripping-vapor-permeation" method (briefly named VSVP) for online separation and purification of butanol, acetone and ethanol from a broth of the fermentation;

wherein the VSVP method comprises the following steps:
a. introducing a gas bubble into the fermentation broth to vaporize ABE or Butanol;
b. subjecting the gas along with the vaporized ABE or Butanol to a membrane separation unit to pass through the membrane;
c. recovering ABE or Butanol, or subjecting ABE or Butanol to a next separation device.

2. The method according to item 1, wherein the gas bubble is derived from a self-produced gas (off-gas) of the Acetone-butanol-producing bacterium or a butanol-producing bacterium or from a foreign source, and wherein the self-produced gas is preferably carbon dioxide and/or hydrogen; the gas from a foreign source is preferably nitrogen.

3. The method according to item 1, wherein the Acetone-butanol-producing bacterium is preferably selected from the group consisting of *Clostridium acetobutylicum*, *Clostridium beijerinckii*, *E. coli*, *Clostridium tyrobutyricum*, and an genetically engineered strain therefrom, preferably is *Clostridium acetobutylicum*; the butanol-producing strain is an genetically engineered bacterium producing butanol, preferably a butanol-producing *E. coli* or a butanol-producing *Clostridium*.

4. The method according to item 1, wherein the membrane is a vapor permeation membrane that ABE or Butanol at feed side, permeate side of the membrane and through the membrane are in vapor form, preferably an organic hydrophobic membrane or an organic and inorganic composite membrane with high selectivity to butanol and acetone, more preferably at least one selected from the group consisting of silicone, poly[1-(trimethylsilyl)-1-propyne], polypropylene, polybutadiene, polyvinylidene fluoride, polytetrafluoroethylene or a derivative thereof, Nitrile Butadiene Rubber, and molecular sieve material, most preferably a composite membrane containing polydimethylsiloxane (PDMS); the membrane is preferably a tubular membrane, a wound membrane, a plate membrane, or a hollow fiber membrane.

5. The method according to item 1, wherein the recovery is carried out through condensation, preferably using a cooling device, liquid nitrogen or cooling water, wherein the cooling temperature using the cooling device is −30-+15° C.

6. The method according to item 1, wherein the gas bubble is introduced from the bottom of a bioreactor with a gas volume in the range of 0.5-5 vvm.

7. The method according to item 1, wherein a permeate side of the membrane separation unit keeps a degree of vacuum in the range of 0-10 kpa, preferably <5 kpa.

8. A device for fermentation integrated with separation and purification of acetone, butanol, and ethanol (ABE) or butanol alone, comprising:

a medium tank (1), used for supplying a medium into a bioreactor;

a bioreactor (2), connected with the medium tank (1), used for fermentation;

a gas distributor (9), used for supplying gas bubble to the fermentation broth;

a membrane separation unit (4), with gas communication to the bioreactor (2), used for receiving a gas with ABE or butanol vapor from the bioreactor and separating ABE or butanol;

a condensation unit (5), used for recovering ABE or butanol vapor into liquid form;

a vacuum manometer (6) and a vacuum pump (8), used for supplying a force for driving ABE or butanol permeate through the membrane in a vapor form;

a product tank (7), used for receiving a product in liquid form.

9. The device according to item 8, further comprising a pump (3) used for circulating the gas in the membrane separation unit (4) back to the bioreactor (2).

10. The device according to item 8, wherein the membrane in the membrane separation unit (4) is a vapor permeation membrane, preferably an organic hydrophobic membrane or an organic and inorganic composite membrane with high selectivity to butanol and acetone, more preferably at least one selected from the group consisting of silicone, poly[1-(trimethylsilyl)-1-propyne], polypropylene, polybutadiene, polyvinylidene fluoride, polytetrafluoroethylene or a derivative thereof, Nitrile Butadiene Rubber, and molecular sieve material, most preferably a composite membrane containing polydimethylsiloxane (PDMS); the membrane is preferably a tubular membrane, a wound membrane, a plate membrane, or a hollow fiber membrane. Since the hydrophobic membranes are selected, butanol (ABE) vapor rather than water is/are more selectively preferred to permeate through the membrane.

The purpose of the present disclosure is to provide a method and device for separating and purifying ABE or Butanol with high efficiency. In particular, a method is provided for ABE (or Butanol alone) fermentation integrated with a vapor-stripping-vapor-permeation process for separation and purification of ABE (or Butanol alone). Firstly, an Acetone-butanol-producing bacterium or a butanol-producing bacterium is cultured, and then ABE (or Butanol alone) are obtained by fermentation of the above bacteria; a close-circulating vapor-stripping-vapor-permeation (VSVP) process is used for online recovery of ABE or Butanol. The detailed steps of the VSVP process is described as follows.

A process for vaporizing ABE (or Butanol alone) in the broth comprises introducing gas/bubble into the fermentation system to vaporize ABE or Butanol in the fermentation broth. The gas/bubble may be provided by circulating the strain-produced off-gas between bioreactor and membrane separation unit, which is so-called close-circulation in the system; the gas/bubble carrying vaporized ABE or Butanol is supplied to the membrane separation unit to contact one side of the membrane; vacuum is produced on the other side of the membrane to pass ABE or Butanol through the membrane, which are recovered by condensation or are directly supplied to a next separation device.

In the present disclosure, the Acetone-butanol-producing bacterium/bacteria is/are preferably *Clostridium acetobutylicum*, *Clostridium beijerinckii*, or another Acetone-butanol-producing bacterium, and a genetically engineered strain only producing butanol.

In a preferable embodiment, the fermentation system for Acetone-butanol-producing bacterium or butanol-producing bacterium comprises a bioreactor, a gas distributor at the bottom of the bioreactor, wherein the gas distributor can be united as one with bioreactor or as a unit placed at the bottom of the bioreactor, for dispersing gas into a large number of tiny-size bubbles.

In a preferable embodiment of the VSVP process, the gas is the self-produced gas produced during fermentation of the bacteria such as carbon dioxide and hydrogen; the feed solution is a fermentation broth containing butanol, acetone and ethanol (or only butanol); the gas is introduced into the fermentation system to form bubbles, making butanol, acetone and ethanol (or only butanol) vaporized for membrane separation; a gas from a foreign source such as nitrogen can also be used for vaporizing butanol, acetone and ethanol (or only butanol).

In a preferable embodiment, the membrane used in the VSVP method is a vapor permeation membrane, preferably an organic hydrophobic membrane or an organic and inorganic composite membrane with high selectivity to butanol and acetone; the feed for membrane separation is butanol, acetone and ethanol (or only butanol) vapor from a fermentation broth; the permeated vapor is directly condensed into liquid by a cooling device or liquid nitrogen; when using a cooling device, the temperature may be in the range of −30-+15° C.; on the permeated liquid side of the membrane, a degree of vacuum in the range of <5 kpa is maintained.

Efficiency for production and separation of ABE is improved by using the disclosed method, with saving energy requirement and without increasing device investment, which provides technical support for production and recovery of biologically produced liquid biofuel (mainly butanol and acetone) and biochemicals.

The advantages of the fermentation integrated with close-circulating VSVP technology provided in the present disclosure comprise the following: 1. ABE or Butanol are carried out by introducing gas/bubbles into the bioreactor, and undesirable impurities such as protein, cells, sugars etc. raw material are not involved; 2. The feed for membrane only contains butanol, acetone, ethanol (or butanol) and water vapor and do not contain any other impurities; there is no risk of fouling the membrane and the method in the present disclosure can completely solve membrane fouling problem. 3. The integrated fermentation and VSVP process has a higher butanol selectivity than the sole techniques such as pervaporation and gas stripping because of the vaporized butanol (ABE) on both sides of membrane, and thus can provide a condensed solution of butanol, acetone and ethanol (or butanol) with a higher concentration; 4. The energy consumption of the VSVP process is lower than other processes such as pervaporation and gas stripping. Till now, there is no publication and patent using a VSVP process for butanol and acetone recovery.

SPECIFIC EMBODIMENTS

The present disclosure is a method for ABE or Butanol production and recovery. Firstly, an acetone-butanol-producing bacterium or a butanol-producing bacterium is cultured, and the bacterium is fermented to produce ABE or Butanol. Secondly, The VSVP process is integrated with fermentation for online ABE or Butanol recovery. Gas/bubbles are introduced from the bottom of bioreactor (fermentation vessel) to vaporize ABE or Butanol, which leave the bioreactor along with the gas/bubble. The gas/bubble is the self-produced gas (off-gas) produced in the pipeline by the bacteria during fermentation process, or is from a foreign source (such as nitrogen). The gas carries the vaporized ABE or Butanol to the membrane separation unit and contacts one side of the membrane. Vacuum is produced on the other side of the membrane to drive ABE or Butanol through the membrane. ABE or Butanol is permeated through the membrane in vapor form, and then recovered by condensation or directly introduced into a next separation device. Accordingly, ABE or Butanol in the gas form is present on both sides of the separation membrane.

Figure 1:
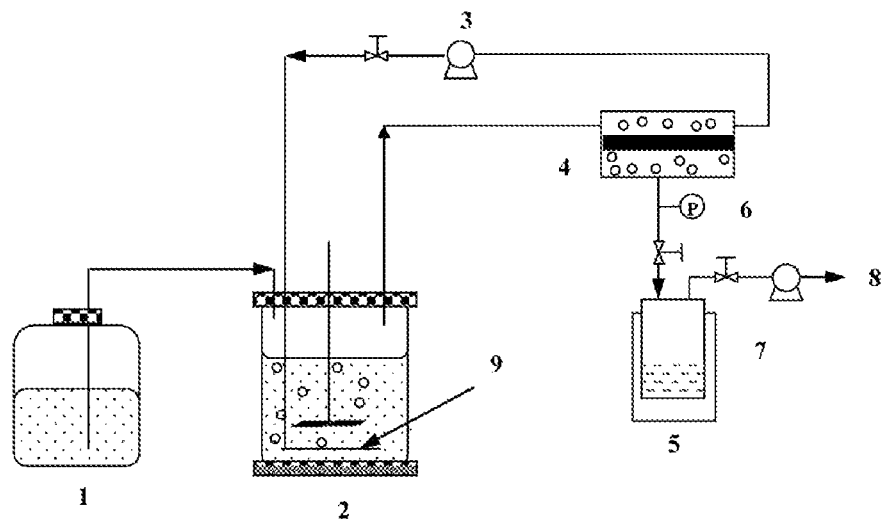
FIG. 1 depicts a device of vapor-stripping-vapor-permeation integrated with fermentation process for ABE or Butanol production with one aspect of the present disclosure. 1: Medium tank; 2: Bioreactor; 3: Pump; 4. Membrane separation unit; 5: Cooling device; 6: Vacuum manometer; 7: Product storage tank; 8. Vacuum pump; 9: Gas distributor.
Figure 2:
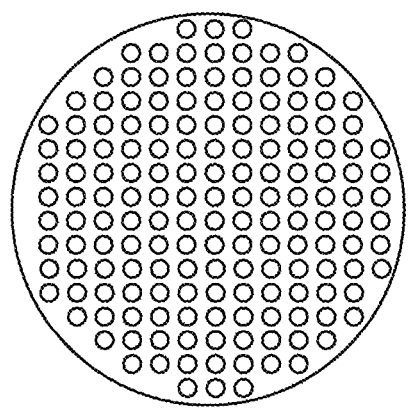
FIG. 2 depicts a gas distributor located at the bottom of the bioreactor.

The process is described in detailed in view of FIG. 1 taking an Acetone-butanol-producing bacterium as an example.

<Acetone-Butanol-Producing Bacterium Culture>

Firstly, in seed culture, seed medium is used for culturing the Acetone-butanol-producing bacterium.

The Acetone-butanol-producing bacterium is not limited, an Acetone-butanol-producing bacterium of Clostridium acetobutylicum, Clostridium beijerinckii, E. coli, Clostridium tyrobutyricum, and a genetically engineered strain therefrom can be used, preferably Clostridium acetobutylicum.

Before using seed medium, preferably nitrogen gas or another inert gas may be introduced into the seed medium for 10 min to remove oxygen, and then sterilization for 30 min at 121° C. Then the medium is cooled to room temperature for strain inoculation of an Acetone-butanol-producing bacterium.

Preferably the Acetone-butanol-producing bacterium is cultured into the actively exponential phase. The culture conditions for culturing the bacterium to exponential phase comprise preferably culture time of 12-18 h, culture temperature of 35-39° C., especially at 37° C.

<Butanol, Acetone and Ethanol Obtained by Fermentation of the Acetone-Butanol-Producing Bacterium>

The seed culture medium comprising the Acetone-butanol-producing bacterium obtained by the above steps is inoculated from the seed culture container into the bioreactor of FIG. 1 (fermentation vessel) for fermentation.

The fermentation broth provides nutrients (carbon source) for the Acetone-butanol-producing bacterium, and glucose can be used as the carbon source of the fermentation broth, while carbon sources such as corn starch, cassava starch, molasses, sucrose, cassava, or stover cellulose hydrolysis solution etc. can also be used.

Preferably, the fermentation broth is sterilized for 30 min at 121° C., treated with nitrogen or another inert gas for 2 h to remove oxygen, cooling to room temperature and then the Acetone-butanol-producing bacterium is inoculated into the fermentation broth.

The inoculation amount of the Acetone-butanol-producing bacterium may be suitably adjusted according to the amount of the broth, generally 5%-10% (v/v) of the fermentation broth volume.

The fermentation temperature is 35-39° C., preferably 37° C. The pH of fermentation is controlled at >5.0. When pH is lower than 5.0, ammonia or sodium hydroxide is added into fermentation broth. When pH is higher than 5.0, it is not required to adjust pH. Alternatively, in fermentation process, it is possible not to adjust the pH and let it change with the fermentation process.

<The Fermentation Integrated with VSVP Process for Online Butanol, Acetone and Ethanol Recovery>

As for VSVP process in the present disclosure, firstly, the method is mainly based on the volatility of butanol, acetone and ethanol and their adsorption on the surface of gas. Online butanol, acetone and ethanol recovery from fermentation broth is realized by butanol, acetone and ethanol volatilization with sparged gas. The butanol, acetone and ethanol are produced during fermentation, and at the same time they are removed from bioreactor. The removal of butanol, acetone and ethanol can be beneficial for decreasing their inhibition to cells and improving butanol, acetone and ethanol production. Secondly, the vaporized butanol, acetone and ethanol can be concentrated and purified with gas. Thirdly, the vaporized butanol, acetone and ethanol also can be concentrated by permeating through a membrane by vacuum driving force. Fourthly, there is no membrane fouling risk since butanol, acetone and ethanol are in a gas form on both sides of the membrane.

In the VSVP process integrated with fermentation, a circulating pump is started for sparging gas into the bioreactor when the butanol concentration in fermentation broth accumulates to a fixed concentration. The circulating pump can allow gas to circulate between the bioreactor and membrane separation unit. On the other side of the membrane, a vacuum pump is started to provide driving force for butanol, acetone and ethanol vapor permeating through the membrane. At the same time, a cooling device is started for vapor condensation.

The gas for vaporization of Butanol and acetone is preferably any off-gas (generally carbon dioxide, hydrogen) produced from fermentation by various strains. The circulation of off-gas between bioreactor and membrane separation unit can recover and concentrate butanol, acetone and ethanol, which has advantage in saving costs and not requirement of gas from a foreign source.

The butanol concentration in the condensate side of the membrane can be up to 20%-30% (w/v), and acetone concentration in the condensate can be up to 10%-15% (w/v).

The preferable conditions for gas sparging in VSVP process is 0.5-5 vvm. Gas may be sparged into the bottom of bioreactor and comes out of the bioreactor from the top. The gas along with butanol, acetone and ethanol vapor flows into the membrane separation unit.

The vapor permeation membrane is fixed in the membrane separation unit. One side of the membrane is the vaporized butanol, acetone and ethanol; the other side of the membrane maintains a certain vacuum. The vaporized butanol, acetone, ethanol and water are selectively permeated through the membrane, and the permeated vapor is collected and condensed in product storage tank by a cooling device.

The permeated condensate containing concentrated buanol, acetone and ethanol can be further purified by distillation, membrane separation, and molecular sieve separation etc. to get purified ABE.

The temperature for membrane separation is 0-80° C., depending on fermentation condition as well as the performance of the membrane. The permeated vapor is usually condensed by cooling water, liquid nitrogen or by a cooling device. The temperature of cooling water or device may be at −30-+15° C. The vacuum in the permeated side of the membrane may be at 0-10 kpa.

The close-circulating VSVP process integrated with fermentation in this disclosure comprises several advantages and merits. It can not only continuously remove the inhibitory ABE or Butanol during fermentation, but also can recover and condense the target products of butanol, acetone and ethanol. Because clean ABE or Butanol vapor is present on both sides of the membrane, there is no membrane fouling risk compared to pervaporation. Therefore, the present disclosure not only improves butanol, acetone and ethanol production efficiency, but also increases the tech-economic of butanol, acetone and ethanol fermentation, which is suitable for industrial application in biobutanol or other biochemical production.

EXAMPLES

The process and device are described in detail using Acetone-butanol-producing bacterium as an example. However, the process and device are not limited by the Examples, and the process and device can be modified in view of the spirits of the invention. Moreover, unless indicated otherwise, the experimental methods are conventional and the material and agents can be purchased readily from a biological or chemical company.

Acetone-butanol-producing bacterium: *Clostridium acetobutylicum*, purchased from ATCC with number of 55025-E604.

Pretreatment of corn stover: Corn stover was ground, passing through a sieve of 0.4 mm. 200 g ground corn stover was suspended in 2% (w/v) NaOH solution at 121° C. for 30 min. The solid residues mainly containing cellulose and hemicellulose were washed and filtrated to neutral pH, and then dried at 50° C. to constant weight. Afterwards, the solid residues were equally divided and each of them was hydrolyzed using cellulose enzyme (0.03 mol/L) at a weight ratio of 1:10. The concentration of the cellulase solution was 0.03 mol/L, and the enzyme buffer was citric acid-sodium citrate Buffer with a pH value of 4.8. The enzyme activity of the cellulase is 20 FPU/g. The reaction was carried out at a speed of 150 r/min for enzymatic hydrolysis 72 h at 50° C. After enzymolysis, the supernatant was obtained by centrifugation at 8000 r/min and adjusted to pH 6.2 with concentrated aqueous ammonia, and 0.115% (w/v) of yeast extract and a mineral mixture containing 0.2 g/L magnesium sulfate 7 $H_2O$, 0.01 g/L ferrous sulfate 7 $H_2O$, 0.01 g/L manganese sulfate monohydrate and 0.01 g/L sodium chloride were added, and then nitrogen was introduced for 5 min, and then sterilization was carried out.

Preparation of corn starch saccharification solution: The corn starch and 60-65° C. warm water at a ratio of 1:2.5 were formulated into a slurry; α-amylase was added according to the proportion of 0.6 ml per kilogram of corn starch, heated to 85-90° C., liquefying for 1-2 hours, then cooling to 60-65° C., adding saccharifying enzyme in a proportion of 1.2 ml per kilogram corn starch, saccharifying for 10-15 hours and filtering to obtain a saccharified liquid. The saccharified solution can be diluted at 1:3 with water for fermentation.

Seed medium: 30 g glucose, 2 g yeast extract, 4 g tryptone, 0.5 g potassium dihydrogen phosphate, 0.5 g dipotassium phosphate, 2.2 g ammonium acetate and mineral mixture were used per liter of culture medium. The mineral mixture comprised: 0.1 g magnesium sulfate 7 $H_2O$, 0.015 g ferrous sulfate 7 $H_2O$, 0.015 g calcium chloride dihydrate, 0.01 g manganese sulfate monohydrate, 0.02 g cobalt chloride and 0.002 g zinc sulfate per liter of culture medium.

Fermentation Medium:

1. Glucose as carbon source: Each liter of medium contained glucose 80 g, yeast powder 1 g, potassium dihydrogen phosphate 0.5 g, dipotassium hydrogen phosphate 0.5 g, ammonium acetate 2.2 g, mineral mixture and vitamins. The composition of the mineral mixture was as follows: 0.2 g magnesium sulfate 7 $H_2O$, 0.01 g ferrous sulfate 7 $H_2O$, 0.01 g manganese sulfate monohydrate and 0.01 g sodium chloride per liter of culture medium; the composition of vitamins was as follows: p-aminobenzoic acid 0.001 g, vitamin B1 0.001 g and biotin 0.00001 g per liter of culture medium.

2. Composition of fermentation broth of corn stover hydrolysate as carbon source: 48.4 g glucose, 15.6 g xylose, 4.8 g cellobiose, 2.4 g arabinose, 1 g yeast powder, 1 g potassium dihydrogen phosphate 0.5 g, dipotassium hydrogen phosphate 0.5 g, ammonium acetate 2.2 g, magnesium sulfate 7 $H_2O$ 0.2 g, ferrous sulfate 7 $H_2O$ 0.01 g, manganese sulfate monohydrate 0.01 g, sodium chloride 0.01 g, p-aminobenzoic acid 0.001 g, 0.001 g vitamin B1 and 0.00001 g biotin per liter of culture medium.

3. Fermentation medium with corn starch as carbon source: 200 g reducing sugar, 0.5 g potassium dihydrogen phosphate, 0.5 g dipotassium hydrogen phosphate, 2.2 g ammonium acetate and 0.2 g magnesium sulfate 7 $H_2O$, 0.01 g ferrous sulfate 7 $H_2O$, 0.01 g manganese sulfate monohydrate, 0.01 g sodium chloride, 0.001 g p-aminobenzoic acid, 0.001 g vitamin B1 and 0.00001 g biotin. The reducing sugar concentration of the corn starch medium at the initial stage of fermentation may be 60-100 g/L, which is diluted by adding water. The concentration of reducing sugar in the corn starch fermentation medium in the batchwise feeding process may be 150-200 g/L.

Acetone-butanol-producing bacterium culture and fermentation: Before using the seed medium, nitrogen was introduced for 10 minutes to remove oxygen, then sterilized at 121° C. for 30 minutes, cooled to room temperature, inoculated with the bacterium. After culturing the bacterium in seed culture at 37° C. for 15 h, they were prepared for introduction into the fermentation medium. Before fermentation, the fermentation medium was sterilized at 121° C. for 30 minutes and then purged with nitrogen for 2 h to remove oxygen. After cooling to room temperature, the seed-containing seed solution (10% of the volume of the fermentation medium) was pumped into the bioreactor and for fermentation at 37° C. The pH was not adjusted in the initial fermentation medium; when the pH of the fermentation medium was below 5.0, the pH adjusted to 5.0 or more by automatic addition of aqueous sodium hydroxide solution or ammonia.

The bioreactor may be a stirred bioreactor, an airlift bioreactor, or a standing bioreactor.

Gas Permeation Membrane Preparation: Polydimethylsiloxane (PDMS) was purchased from Dow corning USA. Zeolite Nanomaterial (ZSM-5) was purchased from Zeolyst International, USA. ZSM-5 was first dried at 80° C. for 24 hours. The polydimethylsiloxane (PDMS) base fluid and curing agent were mixed at a 10:1 ratio. For the preparation of pure PDMS polymeric membrane, it was centrifuged directly at 8000 rpm for 5 minutes for subsequent operation. For the PDMS mixed membrane with ZSM-5, ZSM-5 in a specified weight ratio (20%-80%) was mixed with the PDMS membrane-forming solution at a ratio of 10:1, centrifuged at 8000 rpm for 5 minutes for subsequent operation. The subsequent operation was as follows: film-forming solution was treated for 15 minutes with a sonication to remove the bubble, and then a blade was used to smear the film-forming liquid evenly on the glass plate; the glass with a film-forming liquid was put into the oven at 100° C. for 3 hours for form the film. Finally, the glass plate was taken out of the oven; the prepared gas permeable film was peeled off, fixed in a membrane separation unit, and used for permeation coupled separation and purification operations.

For Butanol, Acetone, Ethanol Analysis, a conventional gas chromatography was used; for assay of the concentration of sugars in solution of glucose, reducing sugars and the hydrolyzate of corn stover, a conventional liquid chromatography or the DNS method was used.

Comparative Example 1: Fermentation of ABE without Coupled Separation Device (No Products Separation)

Acetone-butanol-producing bacterium was cultured and fermented using the above fermentation medium of glucose as a carbon source. When the bacteria were inoculated into the bioreactor, fermentation was started until the end of fermentation. Results were shown in Table 1, the endpoint concentrations of butanol, acetone and ethanol in the fermentation medium were about 14 g/L (1.4%), 7 g/L (0.7%) and 2 g/L (0.2%).

Comparative Example 2: Butanol, Acetone and Ethanol were Produced by Fermentation Coupled with Conventional Gas Stripping The Acetone-butanol-producing bacterium was cultured and fermented as described above. When the bacteria were inoculated into the bioreactor, fermentation was started. Conventional gas stripping coupled fermentation was performed; after the start of fermentation, when the concentration of butanol in the fermentation medium was greater than 5 g/L, the gas stripping device was started. In conventional gas stripping, butanol, acetone and ethanol in fermentation broth was vaporized by sparging gas into bioreactor. Subsequently, the vaporized butanol, acetone and ethanol were condensed as liquid by a condenser. To be highlighted, the condenser has no purification and concentration functions. Results were shown in Table 1, the condensate recovered by gas stripping contained 9.0%-11% butanol (w/v), 3.5%-5.0% (w/v) acetone, 0.5%-1.5% (w/v) ethanol. The condensate concentration of butanol, acetone and ethanol was mainly caused by the concentration change of butanol, acetone and ethanol in the fermentation medium.

Comparative Example 3: The Fermentation Integrated with Pervaporation for Butanol, Acetone and Ethanol Production Acetone-butanol-producing bacterium was cultured and fermented as described above. When the bacteria were inoculated into the bioreactor, fermentation was started. Traditional method of fermentation integrated with pervaporation was used. When the concentration of butanol in the fermentation medium was greater than 5 g/L, pervaporation was started using pure PDMS membrane. During pervaporation, fermentation broth was circulated between bioreactor and membrane module for product recovery. When the fermentation broth contacted the pervaporative membrane, the butanol, acetone and ethanol liquid in fermentation broth dissolved and diffused through the membrane, and the fermentation broth was concentrated and purified. So the feed liquid is on one side of the membrane, and the vapor is on the other side of the membrane. As shown in Table 1, the condensate obtained from conventional pervaporation using pure PDMS membrane contained 7.5%-9.0% (w/v), 3.0%-4.0% (w/v) and 0.6%-1.0% (w/v) of butanol, acetone and ethanol. Using PDMS/50% ZSM-5 membrane for pervaporation, the condensate contained 14.0%-18.0% (w/v), 6.0%-9.0% (w/v) and 1.0%-2.0% (w/v) of butanol, acetone and ethanol. The butanol, acetone and ethanol concentrations in condensate were depended on their concentrations in fermentation broth.

Example 1: Using Glucose as Carbon Source in Fermentation Broth, the Fermentation Integrated with VSVP Process was Carried Out Acetone-butanol-producing bacterium was cultured and fermented as described above. When the bacterium entered the bioreactor, fermentation was started. When the concentration of butanol in the fermentation medium was greater than 5 g/L, the VSVP process was started by turning on the pump between bioreactor and membrane separation unit, introducing gas into the bioreactor. The pump made the gas and the vaporized butanol, acetone and ethanol carried with the gas circulate in the closed space formed by the bioreactor and the membrane separation unit. When the vaporized butanol, acetone and ethanol passed through one side of the separation membrane, they dissolved and diffused to the other side of the membrane and were concentrated and recovered by condensation. When the glucose concentration in the fermentation medium dropped below 10 g/L, 400 g/L of concentrated glucose was added to the fermentation medium to continue the fermentation. Since butanol, acetone and ethanol were continuously recovered from the bioreactor by the VSVP process, there was sufficient glucose carbon source in the fermentation medium, and the fermentation could be sustained stably for more than 150 hours. The concentrations of butanol, acetone and ethanol in the condensate obtained by the VSVP process using a pure PDMS polymer membrane were 20.0%-24.0% (w/v), 8.0%-12.0% (w/v) and 0.8%-12.0% (w/v). The concentration of butanol, acetone and ethanol in the condensate obtained by VSVP using a PDMS/50% ZSM-5 membrane were 28.0%-32.0% (w/v), 11.0%-15.0% (w/v) and 1.0%-2.0% (w/v). As can be seen, compared to the gas stripping coupled fermentation of Comparative Example 2, the concentration of butanol and acetone in the condensate obtained by the VSVP method increased by >200%, and ethanol increased by ~100%. Compared with the pervaporation of Comparative Example 3, the concentrations of butanol and acetone in the condensate obtained by the VSVP method increased by about two-fold and the ethanol concentration was almost not changed. In addition, the addition of hydrophobic particles ZSM-5 to the PDMS membrane can increase the separation and purification concentration of butanol and acetone and improve the membrane selectivity. Addition of other nano-hydrophobic particles to the membrane can also improve the separation efficiency of butanol and acetone.

Example 2: Using Corn Stover Hydrolysate as Carbon Source in Fermentation Medium, the Fermentation Integrated with VSVP Process was Carried Out to Produce ABE Acetone-butanol-producing bacterium was cultured and fermented as described above. When the bacteria were inoculated into the bioreactor, fermentation was started. When the concentration of butanol in the fermentation medium was greater than 5 g/L, the VSVP process was started by turning on the pump between bioreactor and membrane separation unit, introducing gas into the bioreactor. The pump made the gas and the vaporized butanol, acetone and ethanol carried with the gas circulate in the closed space formed by the bioreactor and the membrane separation unit. When the vaporized butanol, acetone and ethanol passed through one side of the separation membrane, they dissolved and diffused to the other side of the membrane and were concentrated and recovered by condensation. When the glucose concentration in the fermentation medium dropped below 10 g/L, corn stover hydrolysate was added to the fermentation medium to continue the fermentation. Since butanol, acetone and ethanol were continuously recovered from the bioreactor by the VSVP process, there was sufficient carbon source in the fermentation medium, and the fermentation could be sustained stably. The concentrations of butanol, acetone and ethanol in the condensate obtained by the VSVP process using a pure PDMS polymer membrane were 14.0%-18.0% (w/v), 6.0%-9.0% (w/v), and 0.6% 1.0% (w/v). The concentration of butanol, acetone and ethanol in the condensate obtained by VSVP using a PDMS/ 50% ZSM-5 membrane were 18.0%-22.0% (w/v), 7.0%-11.0% (w/v) and 1.0%-1.5% (w/v). As can be seen, compared to the gas stripping coupled fermentation of Comparative Example 2 and the pervaporaton of Comparative Example 3, the concentration of butanol and acetone in the condensate obtained by the VSVP method were significantly increased, indicating the VSVP can separate and obtain butanol and acetone at significantly higher concentrations and has a significantly higher selectivity and a better separation effect for butanol and acetone. Compared with the fermentation medium using glucose as the carbon source, corn stover hydrolysate may contain inhibitory compounds and may be toxic to the cells and affect production of butanol and acetone. The concentrations of butanol and acetone in fermentation broth are closely related to the concentrations of butanol and acetone in the condensate obtained by VSVP process, that is, if the concentrations of butanol and acetone in fermentation broth are low, the concentration of the butanol permeated to the condensate is also low.

Example 3: Using Corn Starch as Carbon Source in Fermentation Medium, the Fermentation Integrated with VSVP Process was Carried Out to Produce ABE Acetone-butanol-producing bacterium was cultured and fermented as described above. When the bacterium entered the bioreactor, fermentation was started. When the concentration of butanol in the fermentation medium was greater than 5 g/L, the VSVP process was started by turning on the pump between bioreactor and membrane separation unit, introducing gas into the bioreactor. The pump made the gas and the vaporized butanol, acetone and ethanol carried with the gas circulate in the closed space formed by the bioreactor and the membrane separation unit. When the vaporized butanol, acetone and ethanol passed through one side of the separation membrane, they dissolved and diffused to the other side of the membrane and were concentrated and recovered by condensation. When the glucose concentration in the fermentation medium dropped below 10 g/L, corn starch was added to the fermentation medium to continue the fermentation. Since butanol, acetone and ethanol were continuously recovered from the bioreactor by the VSVP process, there was sufficient carbon source in the fermentation medium, and the fermentation could be sustained stably. The concentrations of butanol, acetone and ethanol in the condensate obtained by the VSVP process using a pure PDMS polymer membrane were 17.0%-22.0% (w/v), 7.0%-11.0% (w/v) and 0.7%-1.1% (w/v). The concentration of butanol, acetone and ethanol in the condensate obtained by VSVP using a PDMS/50% ZSM-5 membrane were 22.0%-30.0% (w/v), 9.0%-14.0% (w/v) and 1.0%-1.7% (w/v). As can be seen, compared to the gas stripping coupled fermentation of Comparative Example 2 and the pervaporaton of Comparative Example 3, the concentration of butanol and acetone in the condensate obtained by the VSVP method were significantly increased, indicating the VSVP can separate and obtain butanol and acetone at significantly higher concentrations and has a significantly higher selectivity and a better separation effect for butanol and acetone.

TABLE 1

| | Separation membrane | Butanol concentration (%) | Acetone concentration (%) | Ethanol concentration (%) |
|---|---|---|---|---|
| Comparative Example 1 | | 1.4 | 0.7 | 0.2 |
| Comparative Example 2 | | 9.0-11.0 | 3.5-5.0 | 0.5-1.5 |
| Comparative Example 3 | PDMS | 7.5-9.0 | 3.0-4.0 | 0.6-1.0 |
| | PDMS/50% ZSM-5 | 14.0-18.0 | 6.0-9.0 | 1.0-2.0 |
| Example 1 | PDMS | 20.0-24.0 | 8.0-12.0 | 0.8-1.2 |
| | PDMS/50% ZSM-5 | 28.0-32.0 | 11.0-15.0 | 1.0-2.0 |
| Example 2 | PDMS | 14.0-18.0 | 6.0-9.0 | 0.6-1.0 |
| | PDMS/50% ZSM-5 | 18.0-22.0 | 7.0-11.0 | 1.0-1.5 |
| Example 3 | PDMS | 17.0-22.0 | 7.0-11.0 | 0.7-1.1 |
| | PDMS/50% ZSM-5 | 22.0-30.0 | 9.0-14.0 | 1.0-1.7 |

It can be seen from the above that the concentrations of butanol and acetone in the fermentation broth obtained by the conventional fermentation method without coupled separation process were 1.4%, 0.7% and 0.2%, respectively. The concentrations of butanol and acetone in the fermentation broth obtained by the one-step gas stripping method were about 9.0%-11.0%, 3.5%-5.0% and 0.5%-1.5% respectively. The concentrations of butanol, acetone and ethanol in the condensate obtained by fermentation integrated with pervaporation were 14.0%-18.0% (w/v), 6.0%-9.0% (w/v) and 1.0%-2.0% (w/v) respectively. The one-step VSVP process integrated with fermentation according to the present disclosure can produce butanol, acetone and ethanol of about 28.0%-32.0%, 11.0%-15.0% and 1.0%-2.0%, respectively. It can be seen that the VSVP process can obtain the highest concentrations of the separated and purified products. Since the final product contains very high concentrations of butanol and acetone, pure butanol and acetone are readily obtained by simple dehydration treatments such as rectification, distillation or membrane separation. The VSVP process of the present disclosure is very important for increasing the concentration of butanol and reducing the energy consumption of the whole fermentation and separation process. Compared with the traditional distillation separation, the VSVP method requires energy consumption of about 30% of the traditional distillation separation. Furthermore, it is guaranteed that the subsequent purification of butanol and acetone can be carried out with low energy consumption and high efficiency in a solution rich in butanol and acetone with high concentrations. More importantly, as for the traditional pervaporation method, one side of the pervaporation membrane needs to be contacted with the fermentation broth, wherein the microbial cells, sugars, proteins and other macromolecules in the fermentation broth will foul the membrane during long term of operation, and the cost of cleaning and changing the membrane is very high. In contrast, in the fermentation coupled VSVP process of the present disclosure, vaporized organic solvents are present on both sides of the membrane and there is no foul to the membrane, thereby ensuring the service life (or lifespan) of the membrane. Therefore, the present invention can improve the production and recovery efficiency of butanol and acetone and reduce the energy consumption for separation and purification, and provide a new technology for producing butanol and acetone by a biological method, and has great industrial application value.

The invention claimed is:
1. A method for fermentation integrated with separation and purification of acetone, butanol, and ethanol (ABE) or butanol alone, comprising the following steps:
1) obtaining ABE or butanol by fermentation using an acetone-butanol-producing bacterium or a butanol-producing bacterium;
2) using a "vapor-stripping-vapor-permeation" method (briefly named VSVP) for online separation and purification of butanol, acetone and ethanol, or butanol from a fermentation system continuously producing ABE, or butanol;
wherein the VSVP method comprises the following steps:
a. introducing a gas into the fermentation broth in the fermentation system to produce gas bubbles with vaporized ABE or butanol;
b. passing the gas bubbles with vaporized ABE or the vaporized butanol into a membrane separation unit, to permeate through a membrane in the membrane separation unit in a vapor form;
c. recovering the ABE or the butanol, or subjecting the ABE or the butanol to a next separation device, wherein off gas without cooling from the membrane separation unit is returned to the fermentation system to be used in step a;
wherein the gas is a self-produced gas of the acetone-butanol-producing bacterium or the butanol-producing bacterium.

2. The method according to claim 1, wherein the acetone-butanol-producing bacterium is selected from the group consisting of *Clostridium acetobutylicum, Clostridium beijerinckii, E. coli, Clostridium tyrobutyricum*, and a genetically engineered strain therefrom; the butanol-producing strain is an genetically engineered bacterium producing butanol.

3. The method according to claim 1, wherein the membrane is a vapor permeation membrane.

4. The method according to claim 1, wherein the recovery is carried out through condensation.

5. The method according to claim 1, wherein the gas bubble is introduced from the bottom of a bioreactor with a gas volume in the range of 0.5-5 vvm.

6. The method according to claim 1, wherein a permeated side of the membrane separation unit keeps a degree of vacuum in the range of 0-10 kpa.

7. The method according to claim 1, wherein the self-produced gas is carbon dioxide and/or hydrogen produced with ABE or butanol by acetone-butanol-producing bacterium.

8. The method according to claim 1, wherein the acetone-butanol-producing bacterium is *Clostridium acetobutylicum*; the butanol-producing strain is a butanol-producing *E. coli* or a butanol-producing *Clostridium*.

9. The method according to claim 1, wherein the membrane is an organic hydrophobic membrane or an organic and inorganic composite membrane with a selectivity to butanol and acetone.

10. The method according to claim 1, wherein the membrane is at least one selected from the group consisting of silicone, poly[1-(trimethylsilyl)-1-propyne], polypropylene, polybutadiene, polyvinylidene fluoride, polytetrafluoroethylene or a derivative thereof, Nitrile Butadiene Rubber, and molecular sieve material.

11. The method according to claim 1, wherein the membrane is a composite membrane containing polydimethylsiloxane (PDMS).

12. The method according to claim 1, wherein the membrane is a tubular membrane, a wound membrane, a plate membrane, or a hollow fiber membrane.

13. The method according to claim 1, wherein the recovery is carried out through condensation using a cooling device, liquid nitrogen or cooling water, wherein the cooling temperature using the cooling device or cooling water is −30° C. to +15° C.

14. The method according to claim 6, wherein a permeated side of the membrane separation unit keeps a degree of vacuum <5 kpa.

* * * * *